US011116619B2

(12) United States Patent
Haverich

(10) Patent No.: US 11,116,619 B2
(45) Date of Patent: Sep. 14, 2021

(54) MEDICAL IMPLANT, MEDICAL DEVICE AND METHOD FOR MAKING A MEDICAL IMPLANT

(71) Applicant: MEDIZINISCHE HOCHSCHULE HANNOVER, Hannover (DE)

(72) Inventor: Axel Haverich, Hannover (DE)

(73) Assignee: Medizinische Hochschule Hannover, Hannover (DE)

( * ) Notice: Subject to any disclaimer, the term of this patent is extended or adjusted under 35 U.S.C. 154(b) by 97 days.

(21) Appl. No.: 16/185,148

(22) Filed: Nov. 9, 2018

(65) Prior Publication Data
US 2019/0076230 A1 Mar. 14, 2019

Related U.S. Application Data

(63) Continuation of application No. 15/121,154, filed as application No. PCT/EP2015/054172 on Feb. 27, 2015, now abandoned.
(Continued)

(51) Int. Cl.
*A61F 2/00* (2006.01)
*B65B 31/02* (2006.01)
(Continued)

(52) U.S. Cl.
CPC .......... *A61F 2/0095* (2013.01); *A61B 46/10* (2016.02); *A61B 46/13* (2016.02); *A61N 1/375* (2013.01); *A61N 1/37512* (2017.08); *B65B 5/04* (2013.01); *B65B 31/00* (2013.01); *B65B 51/22* (2013.01); *B65B 51/26* (2013.01); *B65D 75/305* (2013.01); *A61B 2017/00526* (2013.01); *A61F 2240/001* (2013.01)

(58) Field of Classification Search
CPC ....... A61F 2/0095; B65B 31/00; B65B 31/02; B65B 31/024; B65B 31/028
USPC .................. 604/403, 408, 438; 53/403, 405; 206/363
See application file for complete search history.

(56) References Cited

U.S. PATENT DOCUMENTS 3,516,223 A * 6/1970 Andersen ................ B29C 65/38
244/151 R
3,726,057 A * 4/1973 Kemble ........... A61B 17/06133
422/40
(Continued)

OTHER PUBLICATIONS

Rose Seavey;"Sterilization of Surgical Implants: Did You Know . . . "; Managing Infection Control pp. 78-95; Nov. 2006.*
(Continued)

*Primary Examiner* — Gloria R Weeks
(74) *Attorney, Agent, or Firm* — W & C IP

(57) ABSTRACT

A medical implant which is vacuum-packed within an air tight cover material and a medical device for making the same is provided. Also described herein is a method for making a medical implant covered by an air tight cover material, comprising the steps of a) providing the medical implant, b) providing sterile cover material in the form of at least one or at least two pieces, c) placing the medical implant within a space surrounded by the at least one or at least two pieces of the cover material, d) creating an underpressure within the space surrounded by the at least one or at least two pieces of the cover material by evacuating air from this space, and e) air tight sealing of the cover material.

16 Claims, 3 Drawing Sheets

Related U.S. Application Data

(60) Provisional application No. 61/948,209, filed on Mar. 5, 2014.

(51) Int. Cl.

| | | |
|---|---|---|
| *A61N 1/375* | (2006.01) | |
| *A61B 46/10* | (2016.01) | |
| *A61B 46/13* | (2016.01) | |
| *B65B 5/04* | (2006.01) | |
| *B65B 31/00* | (2006.01) | |
| *B65B 51/22* | (2006.01) | |
| *B65B 51/26* | (2006.01) | |
| *B65D 75/30* | (2006.01) | |
| *A61B 17/00* | (2006.01) | |

(56) References Cited

U.S. PATENT DOCUMENTS

| | | | |
|---|---|---|---|
| 3,779,375 A * | 12/1973 | Foster | A61B 17/06133 206/227 |
| 3,797,493 A * | 3/1974 | Saudek | B65D 75/68 206/438 |
| 3,815,315 A * | 6/1974 | Glick | A61B 17/06133 206/210 |
| 4,321,781 A * | 3/1982 | Hall | A61F 2/0095 53/427 |
| 4,418,514 A * | 12/1983 | Spann | B65B 31/00 206/524.8 |
| 4,705,042 A * | 11/1987 | Giurtino | A61N 1/3706 607/27 |
| 4,708,241 A * | 11/1987 | Black | A61B 17/06138 206/227 |
| 4,765,125 A * | 8/1988 | Fafournoux | B65B 31/00 53/374.9 |
| 4,777,780 A * | 10/1988 | Holzwarth | B65D 81/268 53/432 |
| 4,915,226 A * | 4/1990 | Keenan | A61F 15/001 2/168 |
| 5,048,678 A * | 9/1991 | Chambers | A61B 17/06138 206/438 |
| 5,086,914 A * | 2/1992 | Mish | A61B 17/06119 206/388 |
| 5,105,942 A * | 4/1992 | van Veen | B65D 75/36 206/363 |
| 5,121,836 A * | 6/1992 | Brown | A61B 17/06138 206/438 |
| 5,271,495 A * | 12/1993 | Alpern | A61B 17/06133 206/380 |
| 5,295,964 A * | 3/1994 | Gauthier | A61J 1/1462 604/113 |
| 5,301,806 A * | 4/1994 | Olson | A41D 19/0068 15/227 |
| 5,357,732 A * | 10/1994 | Markle | A61B 5/145 53/410 |
| 5,383,891 A * | 1/1995 | Walker | A61F 13/00063 206/438 |
| 5,418,022 A * | 5/1995 | Anderson | B29D 22/003 206/439 |
| 5,630,825 A * | 5/1997 | de la Torre | A61B 17/0469 206/339 |
| 5,675,961 A * | 10/1997 | Gerwin | A61B 17/06133 206/380 |
| 6,116,413 A * | 9/2000 | Tabor | A61N 1/0541 206/205 |
| 6,161,695 A * | 12/2000 | Nicolais | A61F 2/0095 206/438 |
| 6,260,699 B1 * | 7/2001 | Kaplan | A01N 37/36 206/339 |
| 6,470,652 B1 * | 10/2002 | Piron | B65B 11/48 53/373.4 |
| 6,889,839 B1 * | 5/2005 | Rosten | B65D 81/075 206/363 |
| 6,996,952 B2 * | 2/2006 | Gupta | A61L 2/07 53/425 |
| 7,289,855 B2 * | 10/2007 | Nghiem | A61B 5/0031 128/897 |
| 7,302,784 B2 * | 12/2007 | Harges | B29C 65/18 53/434 |
| 7,727,206 B2 * | 6/2010 | Gorres | C12Q 1/04 422/400 |
| 8,219,200 B2 * | 7/2012 | Wenger | A61N 1/08 607/36 |
| 8,224,447 B2 * | 7/2012 | Wenger | A61N 1/372 607/36 |
| 8,391,987 B2 * | 3/2013 | Faraji | A61N 1/375 607/54 |
| 8,668,681 B2 * | 3/2014 | Shimizu | A61J 1/10 206/219 |
| 9,095,324 B2 * | 8/2015 | Peck | A61B 19/026 |
| 9,155,606 B2 * | 10/2015 | Benoit | A61F 2/0063 |
| 2004/0187438 A1 * | 9/2004 | Clarke | A61F 2/0095 53/400 |
| 2005/0077197 A1 * | 4/2005 | Detruit | A61F 2/0063 206/363 |
| 2009/0100802 A1 * | 4/2009 | Bush | A61M 5/002 53/434 |
| 2009/0165793 A1 * | 7/2009 | Peck | A61B 50/30 128/204.17 |
| 2010/0078336 A1 * | 4/2010 | Reyhan | A61B 17/06114 206/63.3 |
| 2011/0192744 A1 * | 8/2011 | Parker | A61B 50/30 206/363 |
| 2012/0037525 A1 * | 2/2012 | Peck | A61M 25/002 206/364 |
| 2014/0021088 A1 * | 1/2014 | Konig | A61J 1/035 206/570 |
| 2014/0046451 A1 * | 2/2014 | Liccardo | A61F 2/0095 623/19.14 |
| 2015/0328468 A1 * | 11/2015 | Moulder | A61N 1/37217 607/27 |
| 2015/0351893 A1 * | 12/2015 | Smith | A61F 2/0095 623/16.11 |
| 2017/0080211 A1 * | 3/2017 | Walling | A61N 1/0541 |
| 2018/0064835 A1 * | 3/2018 | Young | A61L 2/18 |
| 2018/0222655 A1 * | 8/2018 | Grabowski | B65B 5/045 |
| 2018/0256783 A1 * | 9/2018 | Matheny | A61L 27/3629 |

OTHER PUBLICATIONS

Tosei Corporation; "Vacuum Packaging: Industrial Vacuum Packaging"; https:www.tosei-corporation.co.jp/english/introduce/pack/industry_packing.html.; 2005-2012.*

"Biocompatible Packaging for Implantable Minaturized Pressure Sensor Device Used for Stent Grafts: Concept and Choice of Materials", Kirsten et al. 2014.*

* cited by examiner

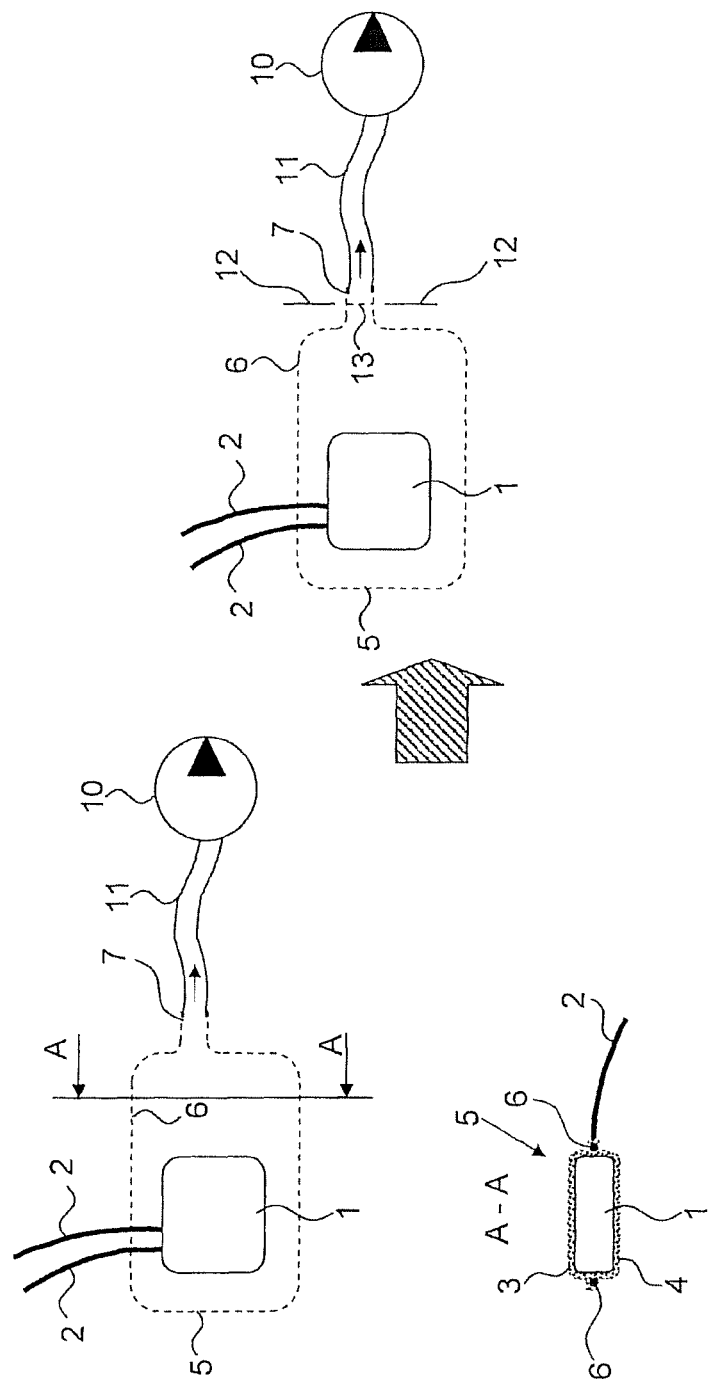

MEDICAL IMPLANT, MEDICAL DEVICE AND METHOD FOR MAKING A MEDICAL IMPLANT

TECHNICAL FIELD OF THE INVENTION

The present invention relates to medical implants of any kind for humans or animals. Such an implant can be e.g. a cardiac pacemaker, as an example for an implant which is widely used in surgery. Another example for such an implant is an endoprosthesis. The invention also relates to a device and a method for making such a medical implant.

BACKGROUND OF THE INVENTION

When implanting a medical implant into a living body, there is always a potential risk of infection. In particular relatively complex implants are difficult to disinfect, e.g. due to a complex shape or, in case of implants with an electrical function, due to cables, cords and so on.

It is therefore an object of the invention to reduce the likelihood of any infection caused by the implantation of a medical implant.

It is another object of the invention to provide for a medical implant, a medical device and a method for making a medical implant which is easy to use and does not require specific skills.

PRIOR ART

WO 2008/136856 A2 discloses resolvable pouches for implantable medical devices. US 2010/0168808 A1 discloses biodegradable polymer-coated surgical meshes formed to pouches for use with cardiac rhythm management devices and other implantable medical devices. U.S. Pat. No. 7,744,915 B2 discloses an apparatus and method for preventing adhesions between an implant and surrounding tissues.

SUMMARY OF THE INVENTION

The present invention provides for an improvement over the prior art proposals by means of the medical implant of claim 1, the medical device of claim 4 and the method for making a medical implant of claim 14. The dependent claims are directed to further embodiments of the invention.

The invention has the advantage that the likelihood of infections due to implantation of a medical implant can be significantly reduced. As a consequence, the need for corrective follow-up surgeries is reduced. By means of vacuum-packing of the medical implant the infection risk can be reduced both by using an appropriate cover material, like an aseptic or sterile material which can in addition be functionalized, e.g. by applying biocide substances to the cover material, e.g. anti-microbial and/or anti-inflammatory substances. The cover material can also be functionalized by creating a certain surface structure, like a certain roughness or a certain relief. The infection risk is further reduced by removing air from the medical implant itself and from the space within the cover material where the medical implant is located in. By the removal of air any negative effects which such air could cause within a living body can be avoided.

As a consequence, the healing process of the patient and the acceptance of the implant within the patient are improved.

Further, the application of the invention is very easy for the user. For example, the packaging of the medical implant within the air tight cover material can be done directly in the operating room, e.g. while the surgery is performed. The medical device for making a medical implant, as defined in claim 4 and the embodiments of the dependent claims, supports the user by making the steps of vacuum-packing of the medical implant very simple.

The underpressure or vacuum to be generated by the underpressure generating device within the space which is surrounded by the cover material can be a vacuum or underpressure of any kind, which means of any pressure level below atmospheric pressure. Therefore, the terms underpressure and vacuum are used as synonyms. Generally it is advantageous to evacuate as much of the air as possible from the space surrounded by the cover material, in order to ensure that any germs and microbes are removed. In practice it is normally sufficient to create an underpressure which is e.g. 20% less than the atmospheric pressure. Generally speaking, any vacuum whether it is low vacuum, medium vacuum, high vacuum, ultra-high vacuum or extremely high-vacuum, is usable for the present invention.

The cover material can be any air tight material which can be closed air tight. It is advantageous to use a cover material which has a sufficient elasticity to be sucked by the underpressure closely to the medical implant, in order to adapt the outer shape of the medical implant. The cover material can be e.g. in the form of a foil made of plastic, rubber, latex or any other biologically compatible material. The cover material can be a bio-resistant material which permanently resists within the patient after implantation. It is also possible to use a bio-degradable cover material. However, in such case it is advantageous to use a bio-degradable cover material which has a long degradation term, e.g. 2 months or more.

According to an advantageous embodiment to the invention, the air tight cover material is a flexible material which rests again the outer surface of the medical implant due to the vacuum within the cover material. By means of the vacuum the cover material can be sucked onto the outer surface of the medical implant and adapts to the outer shape of the medical implant. Compared with prior art proposal, the invention saves space which is required for the medical implant in the body of the patient.

The sealing of the cover can be done one or more of welding, gluing, vulcanizing or any other bonding technology. The sealing can also be done by any kind of form fitting connection technologies, e.g. by providing means for a form fit connection between parts of the cover material, for example through producing a connection like a zip lock, a tongue and groove, a key and slot or a dovetail connection. In any case, the sealing has to be air tight.

The sealing device may comprise at least one welding unit or is a welding unit. Then a welding process is used for sealing the cover material. The sealing is normally done in the form of a weld seam. The weld seam can be produced e.g. by thermal-welding and/or chemical welding.

According to an advantageous embodiment of the invention, the medical device comprises at least a control device which is arranged for automatic control at least of the sealing device in dependence of the underpressure generated by the underpressure generating device. This has the advantage that the user is unburdened from controlling and/or activating the sealing device. For example, the sealing device can be automatically activated in case a certain value of the underpressure is sensed by the control device.

According to an advantageous embodiment of the invention, the medical device comprises exchangeable adapter inserts, wherein the medical implant located within the cover material can be put between the adapter inserts for further modification with the medical device. For example, the medical implant can be located between an upper and a lower adapter insert. This has the advantage that the adapter inserts can be disinfected before use, e.g. by performing a disinfection step or by using prefabricated sterile adapter inserts. As a result, it is not necessary to disinfect the whole medical device. This saves time and effort and makes it easier to use the medical device e.g. during a surgery.

According to an advantageous embodiment of the invention, the adapter inserts are shaped parts which are adapted to the outer shape of the medical implant located within the cover material. This has the advantage that the shaping of the vacuum-packed medical device can be performed and supported by the adapter inserts.

According to an advantageous embodiment of the invention the sealing device comprises at least one welding unit or is a welding unit, wherein the welding unit comprises at least a weld seam producing device for producing a weld seam at the cover material with a defined outline.

According to an advantageous embodiment of the invention the welding unit is arranged for selective creation of heat required for thermal welding of the cover material only in one or more edge areas of the cover material to be welded and is arranged for substantially avoiding heating of the cover material in other areas. This has the advantage that other areas of the cover material as well as the medical implant located therein are not unnecessarily subjected to heat.

According to an advantageous embodiment of the invention the sealing device is arranged for creation of a circumferential sealing seam only on the outer edges of the cover material, so that the cover material is to be provided as a single-layer, non-bag form material, e.g. in the form of at least two pieces, which are connectable to each other by the sealing seam to form a bag.

According to a further embodiment of the invention the sealing device comprises at least a first and a second sealing seam creation device which are separately controllable, whereby different edge areas of the sealing material to be sealed are sealable separately from each other by the first and second sealing seam creation device, in particular at different points in time. The sealing seam produced by the first and/or second sealing seam creation device can be a weld seam.

According to a further embodiment of the invention the medical device comprises at least one control device which is arranged for automatic control at least of sealing device, wherein the control device is arranged for creating a first part of the sealing seam by activating the first sealing seam creation device at a first point in time and for creating a second part of the sealing seam by activating the second sealing seam creation device at a second point in time which is different from the first point in time. This has the advantage that vacuum-packed medical implant can be created in two steps using raw cover material which is provided in non-bag form. In a first sealing step the cover material can be modified into a bag form. Then the vacuum can be applied. The vacuum can be applied permanently until the cover material is completely sealed in an air tight manner in a second sealing step. This avoids that any air could enter again the space which is surrounded by the cover material.

According to a further embodiment of the invention a functionalized cover material is provided as the cover material, in particular in the form of a foil made of plastic, rubber, latex or any other biologically compatible material. The functionalized cover can provide for one or more of the following functions and advantages: supporting the healing process of the patient, supporting the acceptance of the implant within the patient, providing anti-microbial and/or anti-inflammatory support.

According to a further embodiment of the invention a connection stud area for connecting the underpressure creating device is provided on the cover material, and the connection stud area is sealed in an air tight manner after creation of a certain underpressure within the space surrounded by the cover material while the evacuation suction of the underpressure creating device is maintained.

According to a further embodiment of the invention the cover material is provided as at least two separate pieces, the at least two separate pieces are coupled to each other in a first sealing step, which is executed before an underpressure is created within the space surrounded by the cover material, then the underpressure is created and then the cover material is sealed in an air tight manner in a second sealing step. This has the advantage that the raw cover material can be supplied in any suitable form or packaging, like in the form of an endless material on a reel. The cover material can be cut into the required shape by the end user, e.g. by using scissors.

A further advantage is that storage of the raw materials for the cover material is simplified. By using certain standardized pieces of the cover material which are designed for certain kinds of implants and/or diseases, the invention provides for a high flexibility at low efforts (cost and space) for storage of the raw materials. In addition, the flexibility for the end user is maximized. As another advantage, application of the invention does not require complicate or costly devices. The medical device for making the medical implant can be produced at low to medium costs.

The invention can be used for any kind of medical implant. In particular, it is possible to use the invention for medical implants which have one or more cords, like electrical lines or hoses. In such case, according to a further embodiment of the invention one or more cords of the medical implant extend through a sealing seam area of the cover material, wherein a sealing seam is created on the cover material at least in the sealing seam area through which the one or more cords extend.

An advantageous method for making a medical implant covered by an air tight cover material comprises the steps
a) providing the medical implant,
b) providing sterile cover material in the form of at least one or at least two pieces,
c) placing the medical implant within a space surrounded by the at least one or at least two pieces of the cover material,
d) creating an underpressure within the space surrounded by the at least one or at least two pieces of the cover material by evacuating air from this space,
e) air tight sealing of the cover material.

According to a further embodiment of the invention the method is executed less than 30 minutes before implantation of the medical implant. This means that it is possible to execute the method during a surgery.

According to a further embodiment of the invention the cover material is provided in the form of one or more tailored pieces according to the physical dimensions and/or outer shape of the medical implant at least in one viewing direction on the medical implant.

According to a further embodiment of the invention the medical implant located within the space surrounded by the cover material is placed for further modification between at least two exchangeable adapter inserts of the medical device.

According to a further embodiment of the invention the method is executed using the medical device of claim 4.

BRIEF DESCRIPTION OF THE DRAWINGS

Various examples of embodiments of the invention will be described in detail with reference to the following figures, wherein:

FIG. 3 shows a vacuumizing step applied to the medical implant located within the cover material in similar views as FIG. 2, FIG. 4 shows a finalizing step in making a vacuum-packed medical implant in an elevational view.

Figure 2:
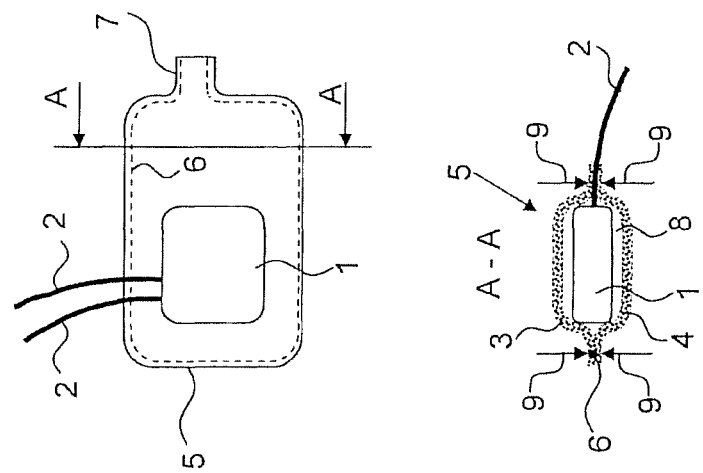
FIG. 2 shows the medical implant within the cover material in an elevational view and a sectional side view.

It should be understood that the drawings are not necessarily to scale. In certain instances, details which are not necessary to the understanding of the invention or render other details difficult to perceive may have been omitted. It should be understood, of course, that the invention is not necessarily limited to the particular embodiments illustrated herein. Same reference numerals are used throughout the drawings.

DETAILED DESCRIPTION OF THE ILLUSTRATED EMBODIMENTS

Figure 1:
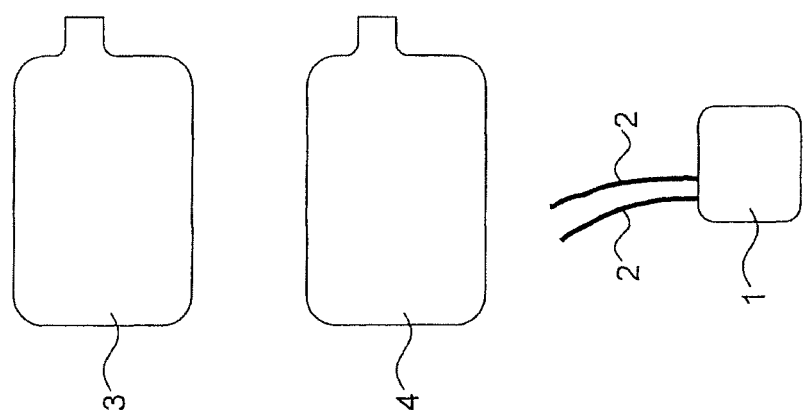
FIG. 1 is an elevational view of a medical implant and its cover material.

FIG. 1 shows a medical device 1, e.g. a cardiac pacemaker, having two cords 2 which are for example electrical lines to be connected to a patient's heart. FIG. 1 further shows two pieces 3, 4 of an air tight functionalized cover material. The pieces 3, 4 were cut from a storage reel of cover material from which the pieces 3, 4 were tailored into the shape shown in FIG. 1.

In the FIGS. 2 and 3, in the upper part an elevational view on the devices is shown and in the lower part a sectional view (section A-A) is shown.

In a next step shown in FIG. 2, the medical implant 1 is placed between the two pieces 3, 4 of the cover material. This creates a space 8 surrounded by the cover material where the medical implant 1 is located in. Now, using a medical device for making a medical implant, a sealing seam 6 is created by a first sealing seam creation device 9, e.g. a thermal welding unit. As can be seen, the sealing seam 6 circumferentially surrounds the medical implant 1 on the outer edges of the pieces 3, 4, thereby creating a stud 7 which is still open. The cords 2 extend through the sealed area between the pieces 3, 4 which is closed by the sealing seam 6.

In a next step shown in FIG. 3, an underpressure generating device 10, e.g. in the form of a pump or any other form of suction device, is coupled e.g. via a hose 11 to the stud 7. Through the underpressure generating device 10 air is evacuated from the space 8, which results in the flexible cover material resting on the outer surface of the medical implant 1.

In a next step shown in FIG. 4 the stud 7 is closed by creating another sealing seam 13 by means of a second sealing seam creation device 12, e.g. again by thermal welding. During the step, the underpressure created by the underpressure generating device 10 is maintained. Once the sealing seam 13 is created, the medical implant 1 is completely enclosed in an air tight manner and therefore vacuum-packed within the cover material 5.

Figure 5:
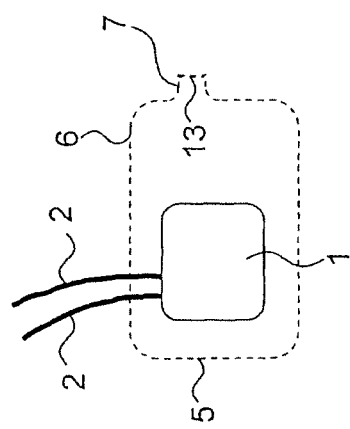
FIG. 5 shows the final vacuum-packed medical implant in an elevational view.

The result is shown in FIG. 5. The vacuum-packed medical implant of FIG. 5 can now be implanted into a patient.

Figure 6:
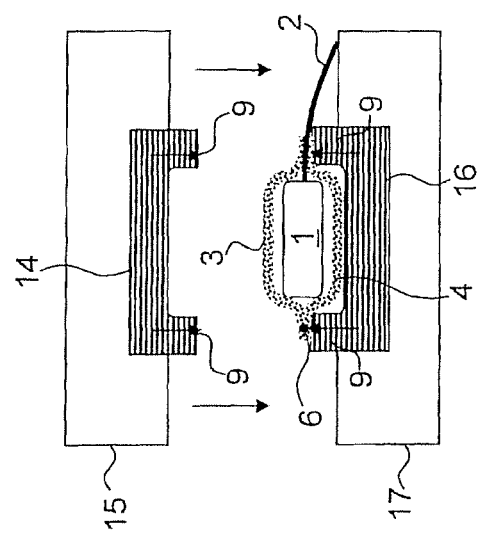
FIG. 6 shows a medical device for making a medical implant covered by an air tight cover material.

FIG. 6 shows in a sectional side view of a medical device for making a medical implant covered by an air tight cover material. The medical device comprises an upper frame 15 and a lower frame 17. In the upper frame 15 an exchangeable upper insert 14 is located. In the lower frame 17 an exchangeable lower insert 16 is located. The two inserts 14, 16 comprise inner openings which are shaped according to the outer shape of the medical implant 1 and/or its surrounding cover material. For performing the steps explained before, the upper frame 15 is moved to the lower frame 17, in order to enclose the medical implant and its surrounding cover material between the inserts 14, 16. Then the first part of the sealing seam can be produced by the first sealing seam creation device 9. Then air is evacuated through the underpressure generating device 10. Then the second sealing seam 13 is produced by the second sealing seam creation device 12. Then the underpressure generating device 10 and its hose 11 can be removed. Then the vacuum-packed medical implant can be taken from the medical device after opening the frames 15, 17. In such a way, the medical device for making a medical implant covered by an air tight cover material can be designed similarly to a waffle iron.

Those reviewing this disclosure will appreciate that various exemplary embodiments have been shown and described, and that according to various exemplary embodiments, features associated with one exemplary embodiment may be used with features included in other exemplary embodiments.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

It is important to note that the construction and arrangement of the battery module having electrochemical cells with integrally formed terminals as shown in the various exemplary embodiments is illustrative only. Although only a few embodiments of the present inventions have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited in the claims. For example, the battery may be non-cylindrical (e.g., oval, rectangular, etc.), the position of elements may be reversed or otherwise varied (e.g., orientation of terminals), and the battery could be a number of different of types (e.g., nickel metal hydride, lithium ion, lithium polymer, etc.). Accordingly, all such modifications are intended to be included within the scope of the present inventions. The order or sequence of any process or method steps may be varied or re-sequenced according to exemplary embodiments. Other substitutions, modifications, changes and omissions may be made in the design, operating conditions and arrangement of the various exemplary embodiments without departing from the scope of the present invention.

The invention claimed is:

1. Method for making a medical implant covered by an air tight cover material and implanting the medical implant within a subject, comprising the steps
    a) providing the medical implant,
    b) providing sterile cover material in the form of at least one or at least two pieces,
    c) placing the medical implant within a space surrounded by the at least one or at least two pieces of the cover material,
    d) creating an underpressure within the space surrounded by the at least one or at least two pieces of the cover material by evacuating air from this space,
    e) air tight sealing of the cover material, wherein the medical implant has one or more cords which extend through a sealing seam area of the cover material, wherein a sealing seam is created on the cover material at least in the sealing seam area through which the one or more cords extend, and
    f) implanting the covered medical implant sealed in step e) within the subject.

2. The method of claim 1, wherein a functionalized cover material is provided as the cover material in the form of a foil made of plastic, rubber, latex or any other biologically compatible material.

3. The method of claim 1, wherein a connection stud area for connecting an underpressure creating device is provided on the cover material, and the connection stud area is sealed in an air tight manner after creation of a certain underpressure within the space surrounded by the cover material while the evacuation suction of the underpressure creating device is maintained.

4. The method of claim 1, wherein the cover material is provided as at least two separate pieces, the at least two separate pieces are coupled to each other in a first sealing step, which is executed before an underpressure is created within the space surrounded by the cover material, then the underpressure is created and then the cover material is sealed in an air tight manner in a second sealing step.

5. The method of claim 1, wherein steps a) through e) are executed less than 30 minutes before implantation of the medical implant.

6. The method of claim 1, wherein the cover material is provided in the form of one or more tailored pieces according to the physical dimensions and/or outer shape of the medical implant at least in one viewing direction on the medical implant.

7. The method of claim 1, wherein the medical implant located within the space surrounded by the cover material is placed for further modification between at least two exchangeable adapter inserts of a medical device.

8. The method of claim 1, wherein the method is executed using a medical device for making a medical implant covered by an air tight cover material, wherein the medical device comprises at least an underpressure generating device and a sealing device, wherein the sealing device is arranged for air tight sealing of the cover material while the medical implant is located within the cover material, wherein the underpressure generating device is coupled or can be coupled with a space which is surrounded by the cover material, and wherein the underpressure generating device and the sealing device are controllable such that after generating a certain underpressure within the space surrounded by the cover material through the underpressure generating device the sealing device is activatable to seal the cover material in an air tight manner to form an air tight protection cover around the medical implant located therein.

9. A method of implanting a medical implant within a subject, comprising the steps
    i) obtaining a covered medical implant made by a method comprising
        a) providing the medical implant,
        b) providing sterile cover material in the form of at least one or at least two pieces,
        c) placing the medical implant within a space surrounded by the at least one or at least two pieces of the cover material,
        d) creating an underpressure within the space surrounded by the at least one or at least two pieces of the cover material by evacuating air from this space, and
        e) air tight sealing of the cover material, wherein the medical implant has one or more cords which extend through a sealing seam area of the cover material, wherein a sealing seam is created on the cover material at least in the sealing seam area through which the one or more cords extend, and
    ii) implanting the covered medical implant within the subject.

10. The method of claim 9, wherein a functionalized cover material is provided as the cover material in the form of a foil made of plastic, rubber, latex or any other biologically compatible material.

11. The method of claim 9, wherein a connection stud area for connecting an underpressure creating device is provided on the cover material, and the connection stud area is sealed in an air tight manner after creation of a certain underpressure within the space surrounded by the cover material while the evacuation suction of the underpressure creating device is maintained.

12. The method of claim 9, wherein the cover material is provided as at least two separate pieces, the at least two separate pieces are coupled to each other in a first sealing step, which is executed before an underpressure is created within the space surrounded by the cover material, then the underpressure is created and then the cover material is sealed in an air tight manner in a second sealing step.

13. The method of claim 9, wherein steps a) through e) are executed less than 30 minutes before implantation of the medical implant.

14. The method of claim 9, wherein the cover material is provided in the form of one or more tailored pieces according to the physical dimensions and/or outer shape of the medical implant at least in one viewing direction on the medical implant.

15. The method of claim 9, wherein the medical implant located within the space surrounded by the cover material is placed for further modification between at least two exchangeable adapter inserts of a medical device.

16. The method of claim 9, wherein steps a) through e) are executed using a medical device for making a medical implant covered by an air tight cover material, wherein the medical device comprises at least an underpressure generating device and a sealing device, wherein the sealing device is arranged for air tight sealing of the cover material while the medical implant is located within the cover material, wherein the underpressure generating device is coupled or can be coupled with a space which is surrounded by the cover material, and wherein the underpressure generating device and the sealing device are controllable such that after generating a certain underpressure within the space surrounded by the cover material through the underpressure generating device the sealing device is activatable to seal the cover material in an air tight manner to form an air tight protection cover around the medical implant located therein.

\* \* \* \* \*